United States Patent [19]

Clark

[11] 4,226,776

[45] Oct. 7, 1980

[54] PREPARATION OF ARYLENE-BIS-MALEIMIDES

[75] Inventor: Raymond D. Clark, Kingsport, Tenn.

[73] Assignee: Eastman Kodak Company, Rochester, N.Y.

[21] Appl. No.: 95,277

[22] Filed: Nov. 19, 1979

[51] Int. Cl.$^3$ .............................................. C07D 403/10

[52] U.S. Cl. .................... 260/326.26; 260/326.5 FM

[58] Field of Search ................. 260/326.26, 326.5 FM

[56] References Cited

U.S. PATENT DOCUMENTS

| T971,003 | 6/1978 | Orphanides | 260/326.26 |
|---|---|---|---|
| 4,154,737 | 5/1979 | Orphanides | 260/326.26 |

OTHER PUBLICATIONS

Lillford et al., J. Chem. Soc. (B), 1967.

*Primary Examiner*—Mark L. Berch
*Attorney, Agent, or Firm*—J. Frederick Thomsen; Daniel B. Reece, III

[57] ABSTRACT

A process for preparing arylene-bis-maleimides by the reaction of an arylenediamine with maleic anhydride followed by treatment of the intermediate compound with acetic anhydride wherein the process is carried out in acetic acid and in the presence of a tertiary amine and the acetic acid to acetic anhydride mole ratio does not exceed 1.3.

1 Claim, No Drawings

PREPARATION OF ARYLENE-BIS-MALEIMIDES

This invention relates to a process for the preparation of arylene-bis-maleimides such as m-phenylene-bis-maleimides.

In the synthesis of arylene-bis-maleimides, an arylenediamine is reacted with maleic anhydride in an inert organic solvent to form an intermediate N,N'-arylenedimaleamic acid which then is treated with a carboxylic acid anhydride to effect ring closure. The most convenient means for isolating the arylene-bis-maleimide is to dilute the reaction mixture with water to achieve maximum precipitation of the product followed by separation of the precipitate from the liquid phase. Such processes are described in U.S. Pat. Nos. 2,444,536, 3,127,414 and 3,522,271. The last-cited reference discloses carrying out the initial diamine-maleic anhydride reaction in the presence of sodium acetate and an organic solvent selected from certain sulfoxides, ketones and carboxamides. Not only are such solvents expensive but their use poses disposal and/or safety problems. Initial attempts to use acetic acid as the solvent were unsuccessful since the use of commercially feasible amounts of acetic acid in the diamine-maleic anhydride reaction in the presence of sodium acetate resulted in an unmanageable thick paste.

I have discovered that the preparation of arylene-bis-maleimides by the reaction of an arylenediamine and maleic anhydride to form a maleamic acid intermediate followed by treatment with acetic anhydride to effect ring closure, i.e., maleimide formation can be carried out in acetic acid as an easily manageable slurry if a tertiary amine such as trimethyl- amine or triethylamine is present in the reaction mixture. I have further discovered that the use of acetic acid as the reaction medium makes the amount of acetic anhydride used per acetic acid present particularly important.

The arylenediamines, the mole ratio of maleic anhydride to arylenediamine and the temperature which may be utilized in practicing my novel process are described in U.S. Pat. No.3,522,271 which is incorporated herein by reference. The amount of acetic acid that is employed as the reaction medium is determined by practical considerations. The lower limit is that amount which can be managed, e.g. stirred, within the particular reaction vessel and under the temperatures used. The use of acetic acid to diamine weight ratios of at least 1.7 usually will give a hetergeneous or homogeneous reaction mixture which is manageable without the use of excessively high temperatures. The upper limit of the amount of acetic acid used depends on a number of factors including the cost of the acetic acid, maximizing equipment usage and the amount of acetic anhydride that will be required in the ring closure step. Generally, the acetic acid to diamine weight ratio will not exceed 3.

The exact identity of the intermediate compound that is treated with acetic anhydride is not known. It is believed to be an equilibrium mixture resulting from the reaction of the tertiary amine and the arylene-bis-maleamic acid which in turn is influenced by the acetic acid present. The amount of acetic anhydride required to give acceptable yields of arylene-bis- maleimide, as mentioned above, is determined by the amount of acetic acid present in the reaction mixture. The acetic acid to acetic anhydride mole ratio should not exceed about 1.3 since higher ratios, e.g. 1.5, give poor yields. Thus, although the stoichiometric amount of anhydride is 2 moles of anhydride per mole of diamine, the anhydride:-diamine ratio will be significantly higher due to the required acid:anhydride ratio. The amount of trimethylamine or triethylamine used in the process should be at least two moles per mole of diamine. While the use of significantly more than two moles is not detrimental to the process, it does not serve any useful purpose.

The practice of the process of my invention is further illustrated by the following examples.

EXAMPLE 1

To a solution of 60 g. of trimethylamine in 100 g. of acetic acid, prepared below 60° C., is added 59 g. of m-phenylene- diamine. The mixture is stirred until everything is in solution which may require heating at 60° C. The mixture is then cooled to 25° C. and 100 g. maleic anhydride is gradually added with cooling as necessary to maintain the temperature below 60° C. When the anhydride-diamine reaction is complete, the reaction mixture is cooled to 25° C. and 200 g. of acetic anhydride is added as rapidly as possible. The exothermic reaction causes the temperature to rise to 60°14 70° C. and a precipitate forms. Stirring is continued for one hour and then the temperature is reduced to 20° C. Water (50 g.) is added and the mixture is stirred for one hour (mild exotherm). The mixture is again cooled to 20° C. and the solid is filtered off, washed twice with acetic acid followed by three washings with water. The solid is then dried. The product (115 g., 85%) melts at 199°–201° C.

EXAMPLE 2

A solution of 98.1 lbs. of maleic anhydride in 40 lbs. of acetic acid is added over a one-hour period to a solution of 59.1 lbs. of trimethylamine and 54.1 lbs. of m-phenylenediamine in 100 lbs. of acetic acid at 40°–45° C. The slurry reaction mixture is stirred for 0.5 hour and then cooled to 25° C. Then 200 lbs. acetic anhydride is added over 1.5 hours at 25°–30° C. The reaction mixture is stirred for 1 hour at 25°–30° C. and then an additional hour at 40°–45° C. followed by cooling to 25° C. Water (50lbs.) is added and stirring is continued for 1 hour. The product is isolated by filtration, washed with water and vacuum dried at 60° C. to give a yield of 80 %.

Although the invention has been described in considerable detail with particular reference to certain preferred embodiments thereof, variations and modifications can be effected within the spirit and scope of the invention.

I claim:

1. In the process for preparing arylene-bis-maleimides by (1) reacting an arylenediamine and maleic anhydride to form an intermediate compound followed by (2) treatment with acetic anhydride, the improvement comprising carrying out reaction (1) in the presence of acetic acid and trimethylamine or triethylamine and the acetic acid to acetic anhydride mole ratio does not exceed 1.3.

* * * * *